United States Patent
Miyamoto et al.

(10) Patent No.: US 9,189,572 B2
(45) Date of Patent: Nov. 17, 2015

(54) SIMULATION DEVICE, SIMULATION SYSTEM, METHOD OF SIMULATION AND PROGRAM

(75) Inventors: Akira Miyamoto, Sendai (JP); Michihisa Koyama, Fukuoka (JP); Kazuki Nakamura, Gifu (JP)

(73) Assignees: IBIDEN CO., LTD., Ogaki-shi (JP); TOHOKU TECHNOARCH CO., LTD., Sendai-shi (JP)

( * ) Notice: Subject to any disclaimer, the term of this patent is extended or adjusted under 35 U.S.C. 154(b) by 528 days.

(21) Appl. No.: 13/638,757

(22) PCT Filed: Mar. 7, 2011

(86) PCT No.: PCT/JP2011/055287
§ 371 (c)(1),
(2), (4) Date: Dec. 7, 2012

(87) PCT Pub. No.: WO2011/122258
PCT Pub. Date: Oct. 6, 2011

(65) Prior Publication Data
US 2013/0132046 A1 May 23, 2013

(30) Foreign Application Priority Data
Mar. 31, 2010 (JP) .................. 2010-083068

(51) Int. Cl.
*G06G 7/50* (2006.01)
*G06F 17/50* (2006.01)
*G01N 15/08* (2006.01)

(52) U.S. Cl.
CPC ........ *G06F 17/5009* (2013.01); *G01N 15/0886* (2013.01)

(58) Field of Classification Search
CPC ........... G06F 17/5009; G01N 15/0886; G01N 15/088
USPC ....................... 703/9, 6, 2; 438/622
See application file for complete search history.

(56) References Cited

U.S. PATENT DOCUMENTS 3,438,245 A * 4/1969 Winslow .................... 73/38
2007/0149627 A1 6/2007 Guan et al.

FOREIGN PATENT DOCUMENTS

| JP | 61 272633 | 12/1986 |
|----|-----------|---------|
| JP | 2004 59904 | 2/2004 |
| JP | 2004 61327 | 2/2004 |

OTHER PUBLICATIONS

Hyvaluoma, J. et al., "Intrusion of Nonwetting Liquid in Paper", Mar. 1, 2007, Physical Review E 75, The Americal Physical Society.*
(Continued)

*Primary Examiner* — Kamini S Shah
*Assistant Examiner* — Cedric D Johnson
(74) *Attorney, Agent, or Firm* — Oblon, McClelland, Maier & Neustadt, L.L.P.

(57) ABSTRACT

A simulation system (101) includes an X-ray CT device (11) that obtains a tomographic image of a porous sample, and a simulation device (14) that simulates a mercury intrusion method by processing a laminated tomographic image of the sample. The simulation device (14) includes a modeling means which processes the laminated tomographic image of the sample, and which models an internal structure of the sample, a minimum-diameter obtaining means that obtains a minimum entrance diameter when mercury enters in a pore of the sample at a predetermined pressure based on a surface energy of the sample and a pressure, and a means that simulates a liquid entering in the interior of the pore from one surface of the sample based on a diameter of the pore of the modeled sample and the minimum entrance diameter.

4 Claims, 14 Drawing Sheets

(56) References Cited

OTHER PUBLICATIONS

Binshan, Ju et al., "A Study of Wettability and Permeability Change Caused by Adsorption of Nanometer Structured Polysilicon on the Surface of Porous Media", Oct. 8-10, 2002, SPE Asia Pacific Oil and Gas Conference and Exhibition, Society of Petroleum Engineers.*
Hilpert, Markus et al., "Pore-Morphology-Based Simulation of Drainage in Totally Wetting Porous Media", 2001, Advances in Water Resources, Elvesier Science Ltd.*
Diamond, Sidney, "Mercury Porosimetry an Inappropriate Method for the Measurement of Pore Size Distributions in Cement-Based Materials", 2000, Cement and Concrete Research 30, Elsevier Science Ltd.*
Garcia-Gabaldon, M. et al., "Effect of Porosity on the Effective Electrical Conductivity of Different Ceramic Membranes Used as Separators in Electrochemical Reactors", Mar. 6, 2006, Journal of Membrane Science 280, Elsevier B.V.*
Koyama, M., et al., "Development of Microstructure Evaluation Method for Porous Electrodes based on Three-Dimensional Porous Structure Simulator," The Electrochemical Society of Japan Taikai Koen Yoshishu, vol. 74, 2C01, p. 86, (Mar. 29, 2007).
Saomoto, H., et al., "Development of Digital Toyoura Porous Model and Porous Media Flow Simulation using SPH," Journal of Applied Mechanics, vol. 9, pp. 649-657, (Aug. 25, 2006) (with English abstract).
Nakashima, Y., et al., "Mathematica Programs for the Analysis of Three-Dimensional Pore Connectivity and Anisotropic Tortuosity of Porous Rocks Using X-ray Computed Tomography Image Data," Journal of Nuclear Science and Technology, vol. 44, No. 9, pp. 1233-1247, (2007).
Hitomi, T., et al., "SPring-8 ni Okeru X-ray CT-zo ni yoru Mortar Bisai Kozo no Kansatsu," Proceedings of the Japan Concrete Institute, vol. 26, No. 1, pp. 645-650, (2004).
Zhu, W.C., et al., "Tracer transport in a fractured chalk: X-ray CT characterization and digital-image-based (DIB) simulation," Transp Porous Media, vol. 70, No. 1, pp. 25-42, (Oct. 2007).
Nakano, T., "Numerical flow simulation through a two-dimensional network using X-ray CT imagery," Bulletin of the Geological Survey of Japan, vol. 46, No. 11, pp. 605-627, (Nov. 1995) (with English abstract).
International Search Report Issued May 24, 2011 in PCT/JP11/55287 Filed Mar. 7, 2011.
Hazlett, Simulation of Capillary-Dominated Displacements in Microtomographic Images of Reservoir Rocks, pp. 21-35, Transport in Porous Media, vol. 20, 1995.†
Hilpert et al., Pore-morphology-based simulation of drainage in totally wetting porous media, pp. 243-255, Advances in Water Resources, vol. 24, 2001.†

\* cited by examiner
† cited by third party

| SAMPLE ID | PHYSICAL PROPERTIES OF SAMPLE INCLUDING SURFACE ENERGY | TOMOGRAPHIC IMAGE |

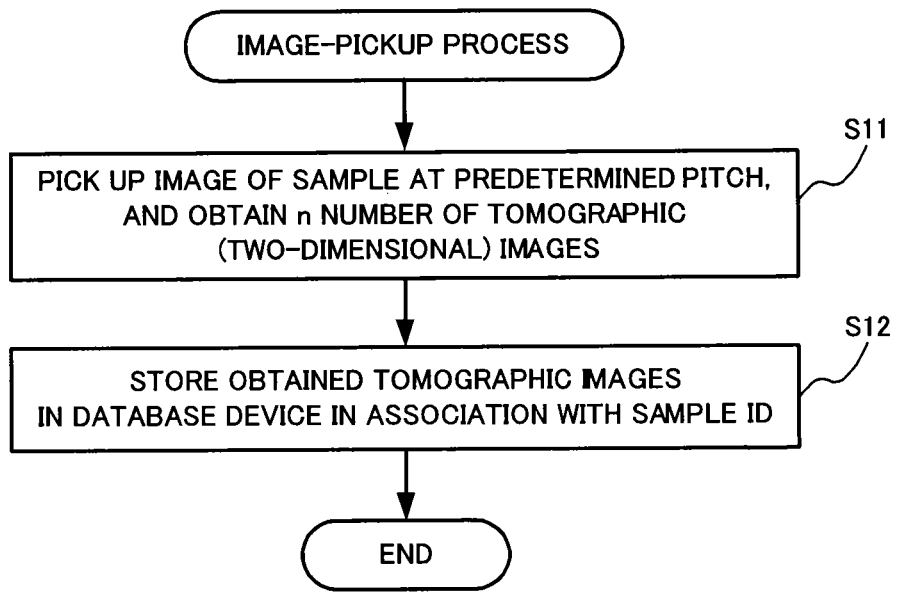
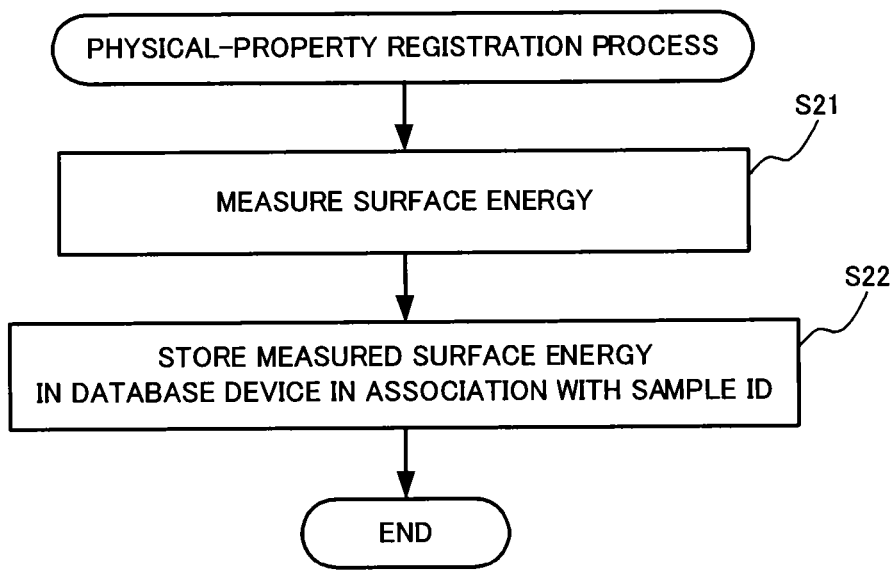

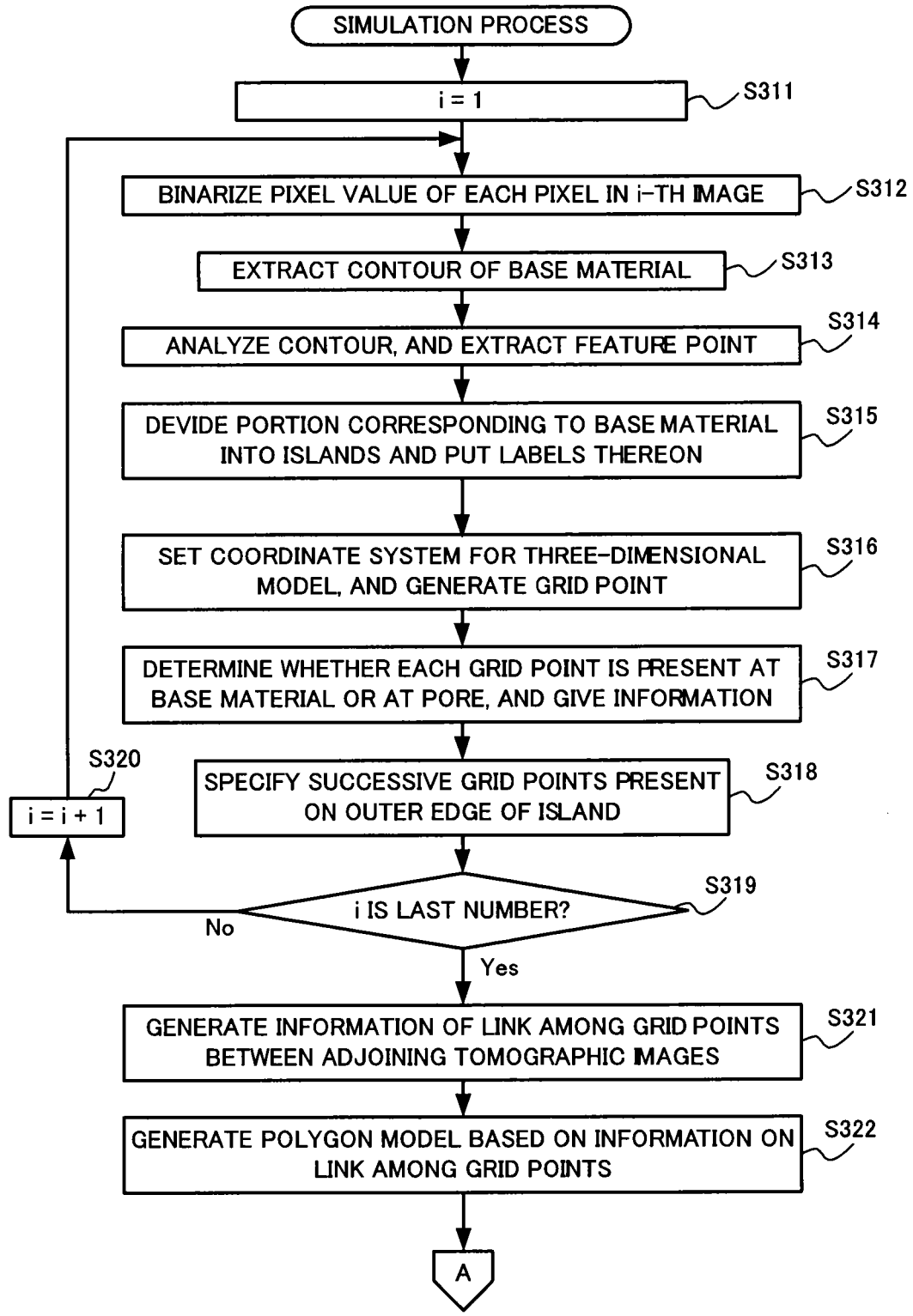

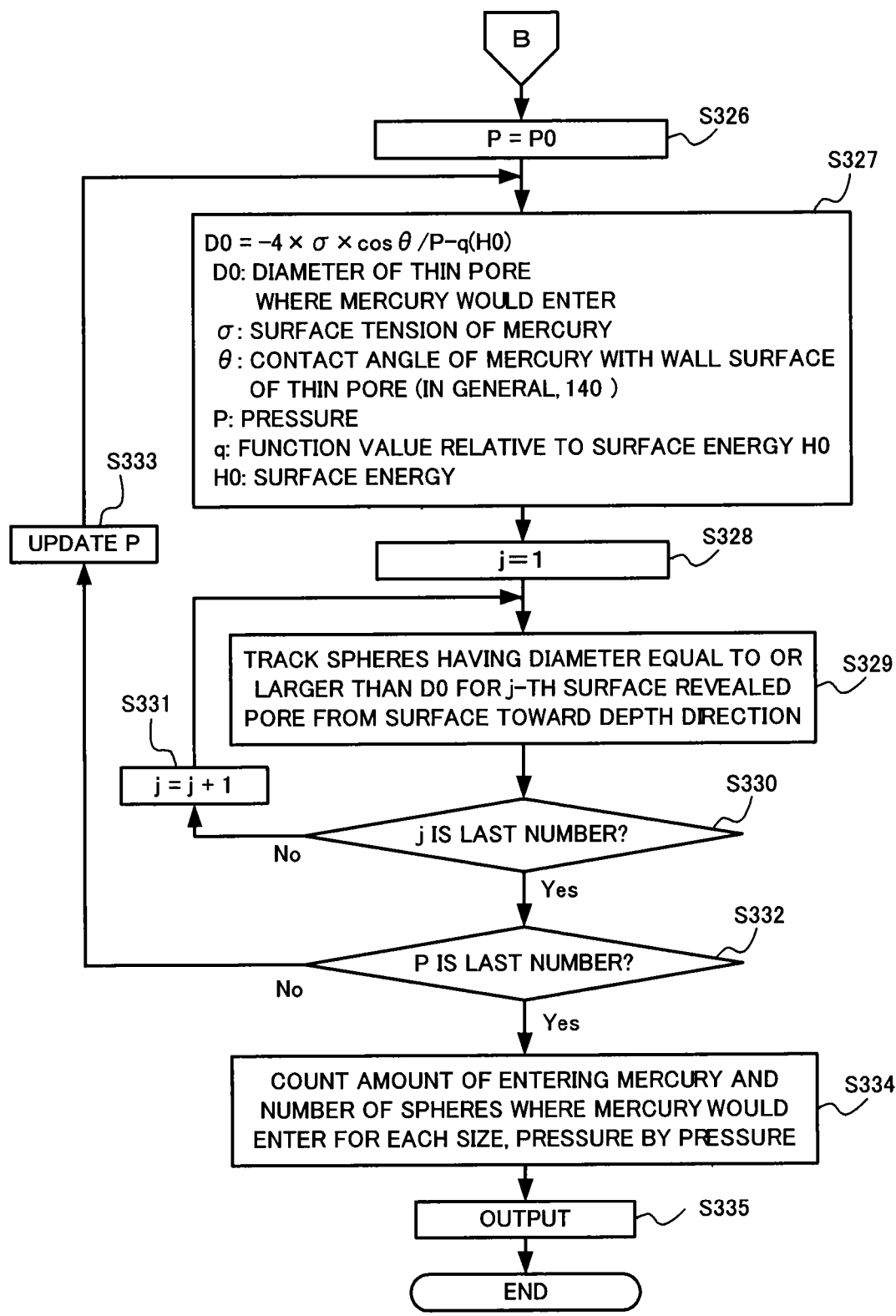

i-TH TOMOGRAPHIC IMAGE i-TH TOMOGRAPHIC IMAGE

SIMULATION DEVICE, SIMULATION SYSTEM, METHOD OF SIMULATION AND PROGRAM

CROSS-REFERENCE TO RELATED APPLICATIONS

The present invention is based on Japanese Patent Application No. 2010-83068 filed on Mar. 31, 2010. The entire specification, claims, and drawings of Japanese Patent Application No. 2010-83068 are herein incorporated in this specification by reference.

TECHNICAL FIELD

The present invention relates to a simulation device, a simulation system, a simulation method, and a program.

BACKGROUND ART

In general, devices utilizing a mercury intrusion method or a bubble point method are applied in order to measure the physical properties of a porous material, such as a porosity, an average pore diameter, and a pore distribution (see, for example, Patent Literature 1).

The mercury intrusion method is a method defined in JIS (Japan Industrial Standards) R 1655 (2003). Moreover, the bubble point method is a method defined in JIS K 3832.

In addition, a method is also known which, for example, obtains a pore diameter through an observation of the surface of a porous material using a microscope.

A DPF (Diesel Particulate Filter) constituted by a porous material represented by ceramics is recently getting attention as a device for eliminating particle-like materials contained in the exhaust gas from a diesel engine.

In the field of the DPF, the average pore diameter, and pore distribution, etc., of a porous material largely affect the functions, such as a pressure loss and a collection efficiency. Hence, data on the average pore diameter, etc., is used to define a product and is also used as guarantee data.

Data obtained through the mercury intrusion method are normally used as data indicating the function of the DPF so far. The use of mercury is, however, restricted in many countries. Moreover, in Europe, the export of mercury is prohibited after 2011, and it is desired to reduce the usage. Accordingly, a measurement through the mercury intrusion method will be restricted from now on, and may become difficult to carry out.

Conversely, the measurement through the bubble point method and the measurement using the microscope differ in the measurement principle from the measurement through the mercury intrusion method. Accordingly, data obtained through the method other than the mercury intrusion method have no correlation with data obtained through the mercury intrusion method. Hence, a measurement through a measuring method equivalent to the mercury intrusion method in principle is needed to maintain the compatibility with past data or products.

In order to address such a disadvantage, a scheme of causing a computer to simulate a measurement through the mercury intrusion method, thereby obtaining a pore diameter, and a pore distribution, etc., is proposed.

PRIOR ART LITERATURE

Patent Literature

Patent Literature 1: Unexamined Japanese Patent Application Kokai Publication No. S61-272633

DISCLOSURE OF THE INVENTION

Problems to be Solved by the Invention

According to the measuring method through a conventional simulation, however, a simulation result does not match with a measurement result obtained through an actual mercury intrusion method, and thus a measurement accuracy (a simulation accuracy) is not high enough.

A similar disadvantage is present in processes of injecting other liquids.

The present invention has been made in view of such disadvantages, and it is an object of the present invention to provide a simulation device, a simulation system, a simulation method, and a program which enable accomplishment of a simulation result that is further closer to a measurement result obtained through the mercury intrusion method.

Means for Solving the Problems

To accomplish the above object, a first aspect of the present invention provides a simulation device that includes a modeling means that processes a tomographic image of a sample and models an internal structure of the sample, a minimum-diameter obtaining means that obtains a minimum diameter of a pore of the sample where a predetermined liquid can enter at a predetermined pressure, and a means that simulates a condition in which the liquid enters in the pore from a surface of the sample based on a diameter of the pore of the modeled sample and the minimum diameter.

The minimum-diameter obtaining means may obtain the minimum diameter of the pore of the sample based on a surface energy of the sample.

The simulation means may include a means which specifies a plurality of spheres in a pore of the modeled sample, and which selects spheres successive from a surface of the sample and having a diameter equal to or larger than the minimum diameter, and a means that calculates an average diameter of the pore of the sample and an amount of the liquid flown into the pore of the sample based on a volume of the selected successive spheres in the pore and a number of the successive spheres for each size.

The minimum-diameter obtaining means may obtain a minimum diameter D0 based on a following formula with a minimum diameter of a pore where a liquid enters being D0, a surface tension of the liquid being σ, a contact angle of the liquid with a wall surface of the pore being θ, a pressure of the liquid being P, a surface energy of the sample being H0, and a function based on the surface energy of the sample being q.

$$D0 = -4 \times \sigma \times \cos\theta / P - q(H0)$$

The liquid may be mercury.

Moreover, a simulation system according to a second aspect of the present invention includes the simulation device of the first aspect of the present invention, and a tomographic-image pickup device which is connected to the simulation device via a communication network, and which picks up a tomographic image of a sample, and/or a measuring device that measures a surface energy of the sample.

Moreover, a simulation method according to a third aspect of the present invention includes a modeling step of processing a tomographic image of a sample and modeling an internal structure of the sample, a minimum-diameter obtaining step of obtaining a minimum diameter of a pore of the sample where a predetermined liquid can enter at a predetermined pressure, and a step of simulating a condition in which the liquid enters in the pore from a surface of the sample based on a diameter of the pore of the modeled sample and the minimum diameter.

Moreover, a program according to a fourth aspect of the present invention causes a computer to function as a modeling means that processes a tomographic image of a sample and models an internal structure of the sample, a minimum-diameter obtaining means that obtains a minimum diameter of a pore of the sample where a predetermined liquid can enter at a predetermined pressure, and a means that simulates a condition in which the liquid enters in the pore from a surface of the sample based on a diameter of the pore of the modeled sample and the minimum diameter.

Effects of the Invention

According to the present invention, a simulation result can be obtained which is further closer to a measurement result obtained through a mercury intrusion method.

BRIEF DESCRIPTION OF DRAWINGS

FIG. 6 is a flowchart for explaining a process of picking up a tomographic image of a sample;

FIG. 7 is a flowchart of a process of registering a measurement result of a surface energy in a database device;

FIG. 8A is a flowchart for mainly explaining a modeling process in a simulation process;

FIG. 8C is a flowchart for mainly explaining a process of simulating an injection process in the simulation process;

FIG. 9D is a diagram showing an example case in which coordinates are set in;

MODE FOR CARRYING OUT THE INVENTION

Embodiments of the present invention will now be explained in detail with reference to the accompanying drawings.

First Embodiment

Figures 1, 2:
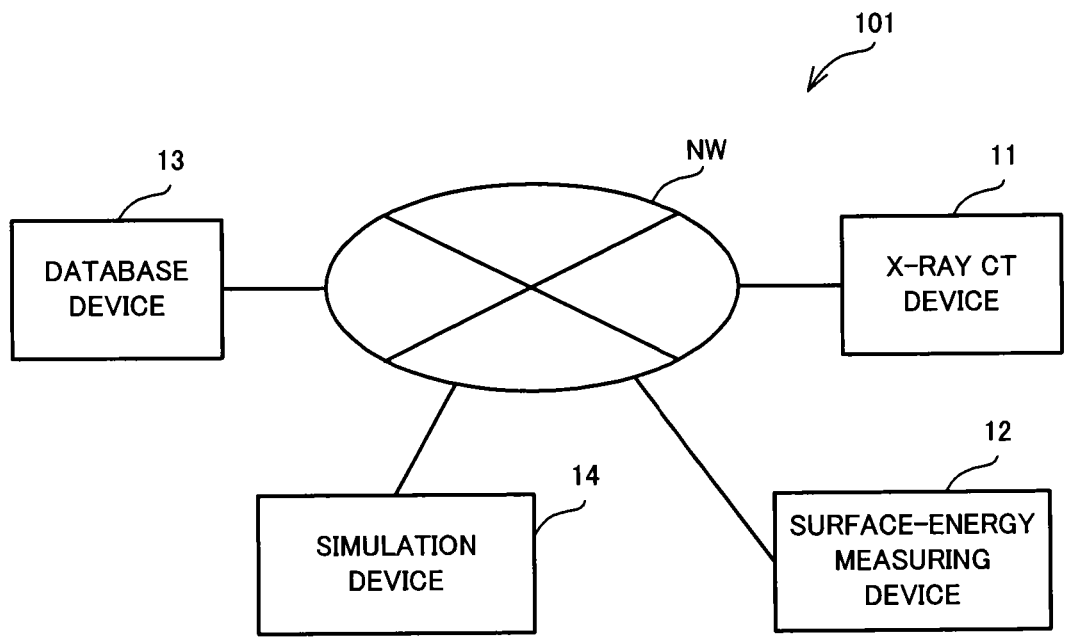
FIG. 1 is a block diagram showing a configuration of a simulation system according to an embodiment.
FIG. 2 is a diagram showing an example data structure stored in a database device shown in FIG. 1.

A simulation system 101 according to this embodiment is a system that simulates a measurement of a pore diameter, etc., of a sample through a mercury intrusion method. As shown in FIG. 1, the simulation system 101 includes an X-ray CT device 11, a database device 13, a surface-energy measuring device 12, a simulation device 14, and a communication network NW that connects those devices with each other.

The X-ray CT device 11 is a device that picks up one or multiple numbers of tomographic images of an object by emitting X-rays thereto. The X-ray CT device 11 picks up an image with a resolution of, for example, 100 nm or so.

The surface-energy measuring device 12 measures wettability (a surface energy) of a sample. The surface-energy measuring device 12 may be a device that obtains a wettability measurement of a sample through a simulation.

As shown in FIG. 2, the database device 13 stores identification data (ID) of a sample, physical properties of the sample including a surface energy, and tomographic images picked up by the X-ray CT device 11 in association with each other.

Figure 3:
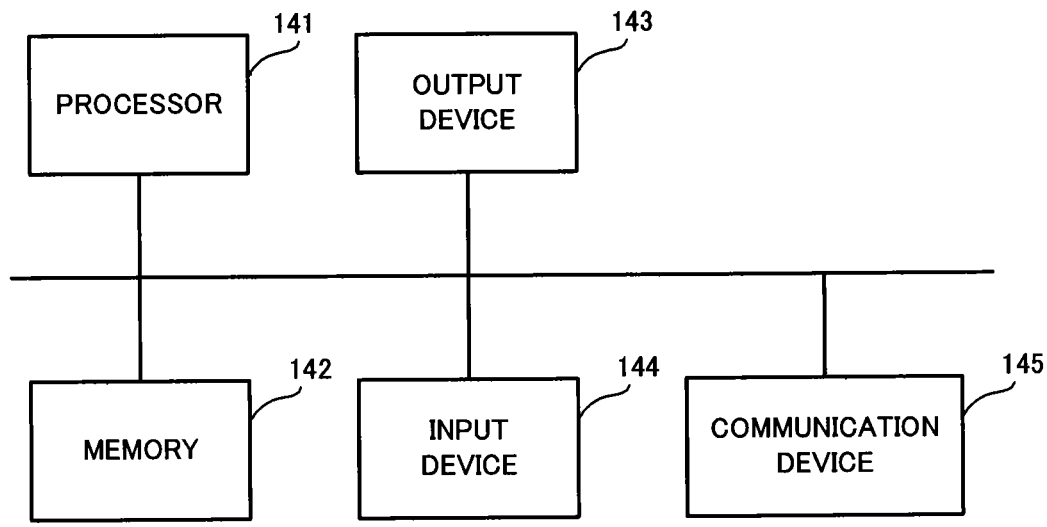
FIG. 3 is a diagram showing an illustrative configuration of a simulation device shown in FIG. 1.
Figure 4:
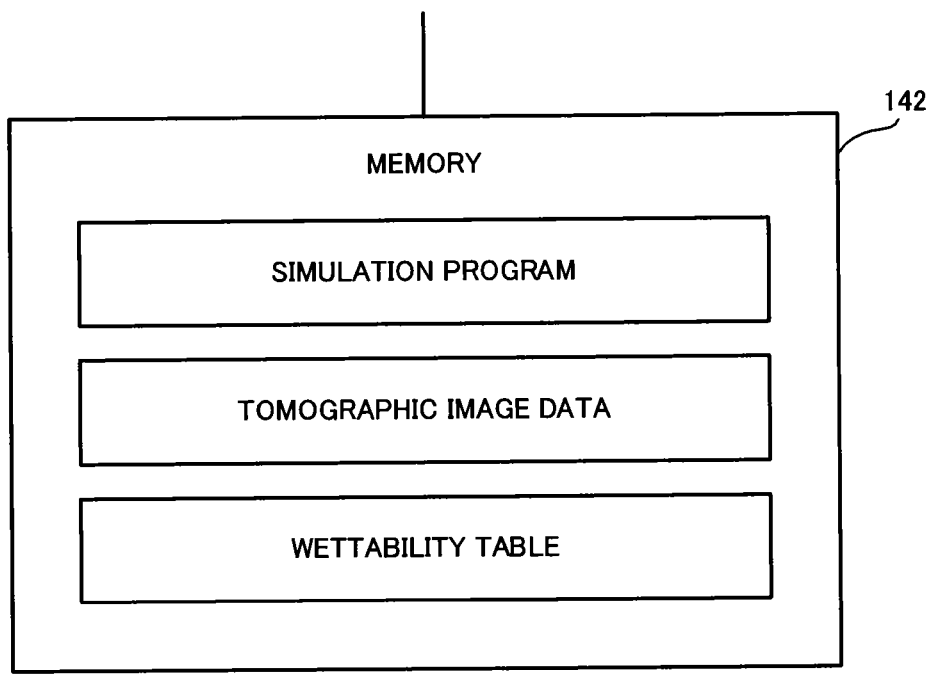
FIG. 4 is a diagram showing an illustrative configuration of a memory shown in FIG. 3.

The simulation device 14 includes a computer. As shown in FIG. 3, the simulation device 14 includes a processor 141, a memory 142, an output device 143, an input device 144, and a communication device 145, etc.

Figure 5:
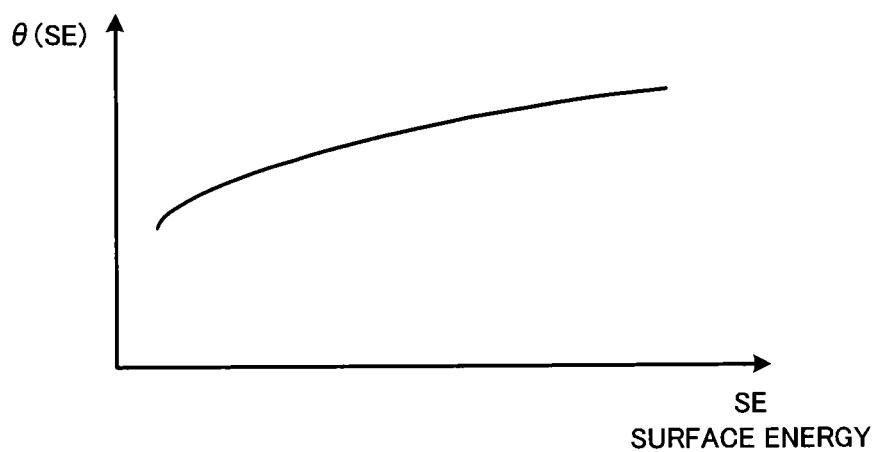
FIG. 5 is a diagram showing an example function of a surface energy of a sample.

The memory 142 stores an operation program for executing a simulation to be discussed later, image data of tomographic images to be processed, and a wettability table, etc. The wettability table is a table that indicates the relationship exemplified in FIG. 5 between a surface energy SE of a sample and a value (a contact angle) θ in a formula (2) to be discussed later. The wettability table can be obtained in advance through, for example, an experiment. The memory 142 also serves as a work area for the processor 141.

The output device 143 includes a display device, and a printer, etc., and outputs various kinds of information.

The input device 144 includes a keyboard, a mouse, and an input device, etc., and receives inputting of various instructions and data.

The communication device 145 communicates with other devices.

The processor 141 includes a one-chip microprocessor, or a CPU board, etc. The processor 141 runs a simulation program stored in the memory 142. The processor 141 also reads a tomographic image of a sample subjected to a measurement from the database device 13, and stores the read image in the memory 142. The processor 141 also processes the tomographic image, and obtains a pore diameter, etc., of a sample.

Next, the specific operation of the simulation system 101 employing the above-explained configuration will be explained.

As explained above, the simulation system 101 is a system that simulates a measurement of a pore diameter, etc., through the mercury intrusion method. The simulation system 101 obtains a diameter, a distribution, and a volume of a pore in a sample.

When attempting to obtain a pore diameter, etc., first, a user cuts a porous material subjected to a measurement into rectangular pieces with a predetermined size to obtain samples. Next, the user sets the sample in the X-ray CT device 11, inputs a sample ID, and instructs an image-pickup.

Figure 9A:
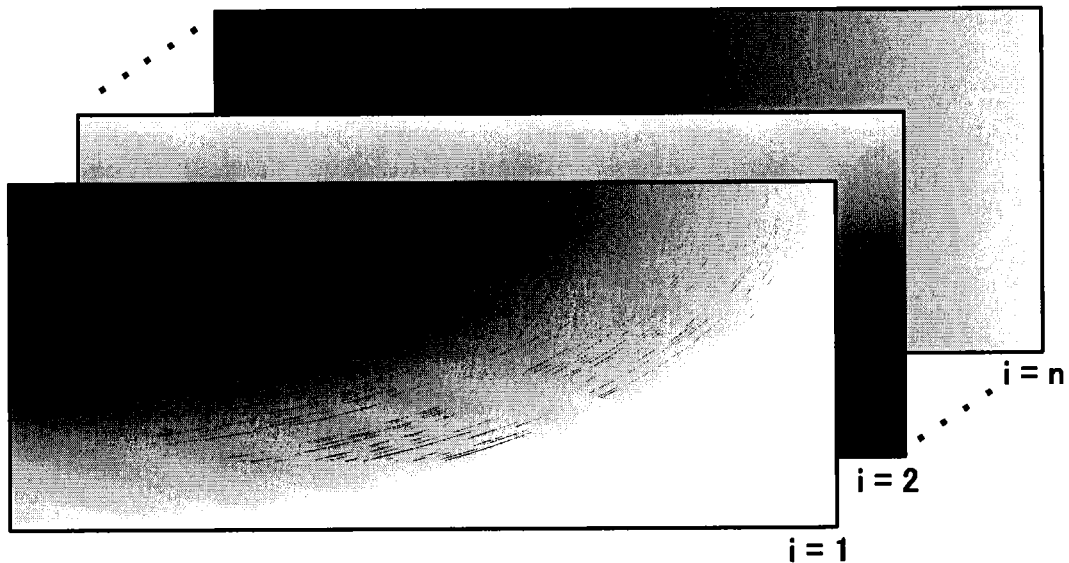
FIG. 9A is a diagram showing an example gradation tomographic image.

In response to such an instruction, the X-ray CT device 11 starts a process shown in FIG. 6. The X-ray CT device 11 picks up plural images of an area including a wall (a surface) of the sample at a predetermined pitch. The X-ray CT device 11 picks up n number of two-dimensional tomographic images (bitmap images) of the sample (step S11). Accordingly, as is exemplified in FIG. 9A, the X-ray CT device 11 obtains three-dimensional gradation image data (voxel data) of a specific area including the surface of the sample.

The X-ray CT device 11 stores the obtained three-dimensional image data in the database device 13 together with the sample ID (step S12).

Next, the user sets the sample in the surface-energy measuring device 12, and inputs the sample ID. The surface-energy measuring device 12 starts a process shown in FIG. 7. First, the surface-energy measuring device 12 measures a surface energy (wettability) of the sample (step S21). Next, the surface-energy measuring device 12 stores the measured surface energy in the database device 13 in association with the sample ID (step S22). Accordingly, as shown in FIG. 2, the database device 13 stores the sample ID, physical properties including a value of the surface energy (the wettability) measured by the surface-energy measuring device 12, and the three-dimensional image data in association with each other. The simulation system 101 may include a simulation device which obtains a wettability value through simulation based on a molecular state of a surface of a sample instead of the surface-energy measuring device 12.

Next, the user inputs the sample ID through the input device 144 of the simulation device 14 to instruct the simulation device 14 to start a simulation.

Figure 8B:
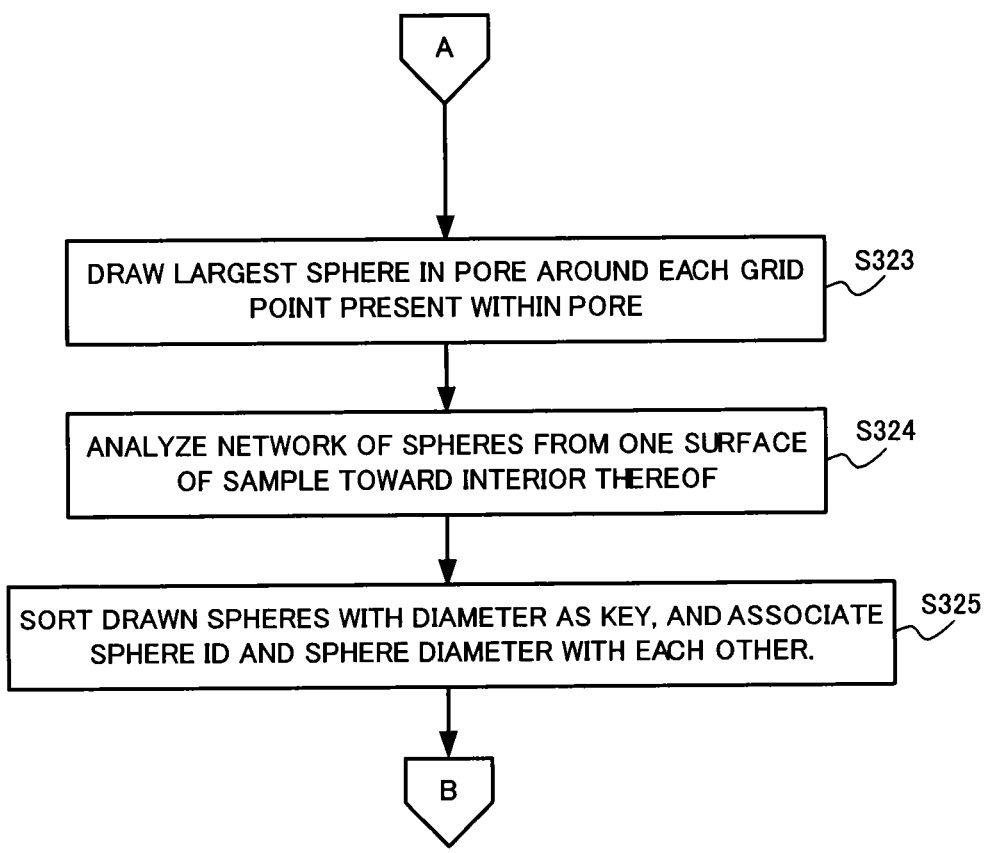
FIG. 8B is a flowchart for mainly explaining a process of drawing spheres corresponding to mercury in a modeled pore in the simulation process.

In response to such an operation, the processor 141 reads the three-dimensional image data of a process target which is identified by the sample ID from the database device 13 through the communication device 145. The processor 141 stores the read data in the memory 142, and executes a simulation process shown in FIGS. 8A to 8C.

First, the processor 141 executes a modeling process of modeling a base material having a pixel value indicated as "1".

In order to facilitate understanding of the present invention, an example of modeling a base material by a polygon model will be explained.

In the modeling process, the processor 141 sets a pointer i that designates a tomographic image number to "1", and picks out an i-th tomographic gradation image (step S311). The processor 141 picks out an i-th tomographic gradation image from, for example, n number of tomographic gradation image data shown in FIG. 9A.

Next, the processor 141 binarizes the i-th picked-out tomographic image (step S312). A binarization method is optional. For example, the processor 141 may divide the i-th tomographic image into a base material having a pixel value of "1" and a pore having a pixel value of "0" with an average of pixel values (CT values) of all pixels of the i-th tomographic image.

Figure 9B:
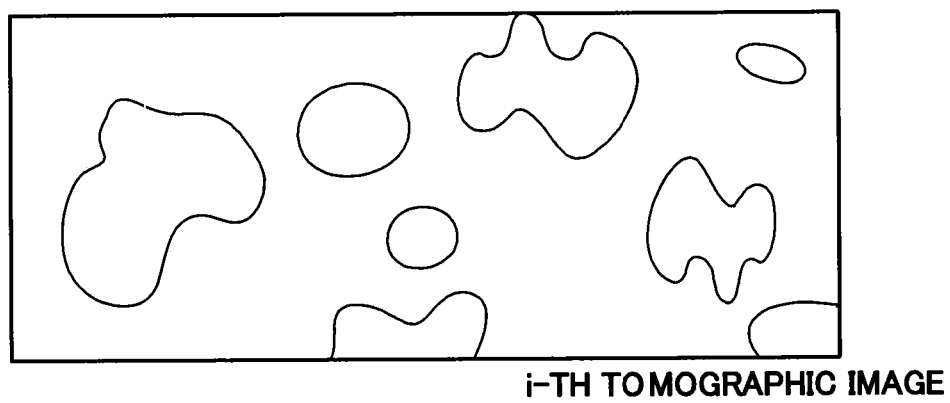
FIG. 9B is a diagram showing an example image emphasizing edges (of a base material)

Next, the processor 141 extracts a contour of the base material of the binarized two-dimensional tomographic image (step S313). As is exemplified in FIG. 9B, the processor 141 obtains a boundary between an area having a pixel value of "1" and an area having a pixel value of "0" through, for example, a Sobel filtering process. Accordingly, the processor 141 obtains the contour of the base material having the pixel value of "1".

Next, the processor 141 obtains feature points of the obtained contour (step S314). The kinds of the feature points are optional. For example, the processor 141 takes an end point, an intersection, a branched point, and an angular point, etc., of the extracted contour as feature points.

Figure 9C:
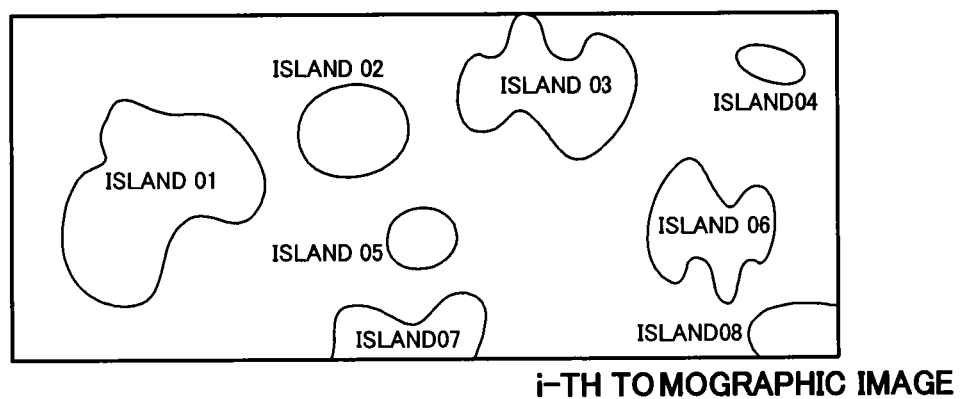
FIG. 9C is a diagram showing a condition with island areas being identified.

Subsequently, the processor 141 identifies an island of an area having a pixel value of "1" over the cross-sectional image based on the extracted feature points and the pixel values, etc., of respective pixels. As shown in FIG. 9C, a label for an identification is put on the island by the processor 141 (step S315).

Figure 9D:
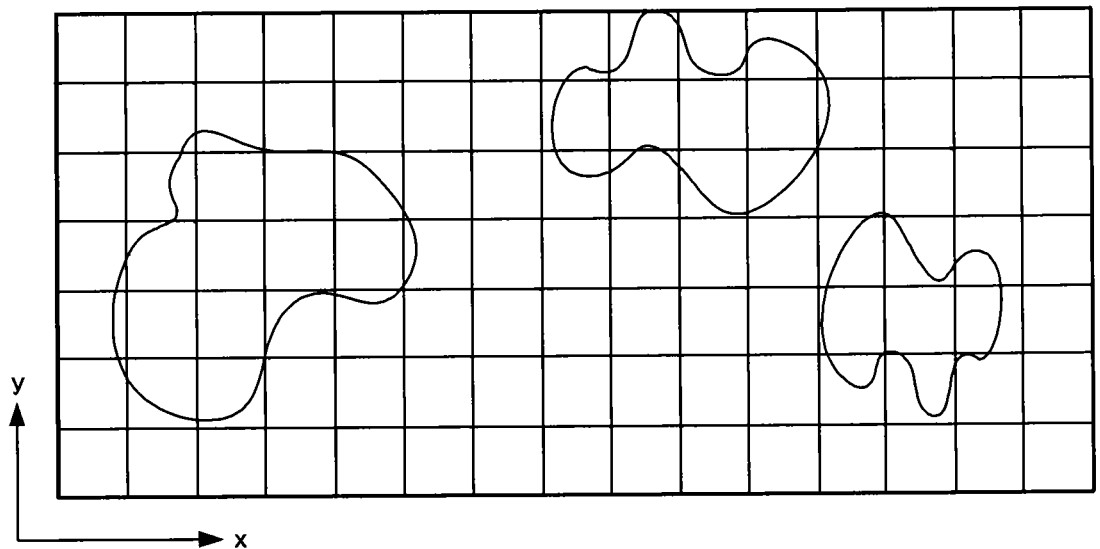

Subsequently, as shown in FIG. 9D, the processor 141 sets a coordinate system (X, Y, Z) for a three-dimensional model on the two-dimensional tomographic image. That is, the processor 141 generates grid points ((X, Y) coordinate points) on a process-target tomographic image (step S316). It is unnecessary that the aligned direction of pixels and an x-axis direction or a y-axis direction are consistent with each other.

Next, the processor 141 determines whether the pixel of each grid point is present within the base material or within a pore based on the pixel value of the pixel on each grid point (or a pixel closest to each grid point) (step S317).

Figure 9E:
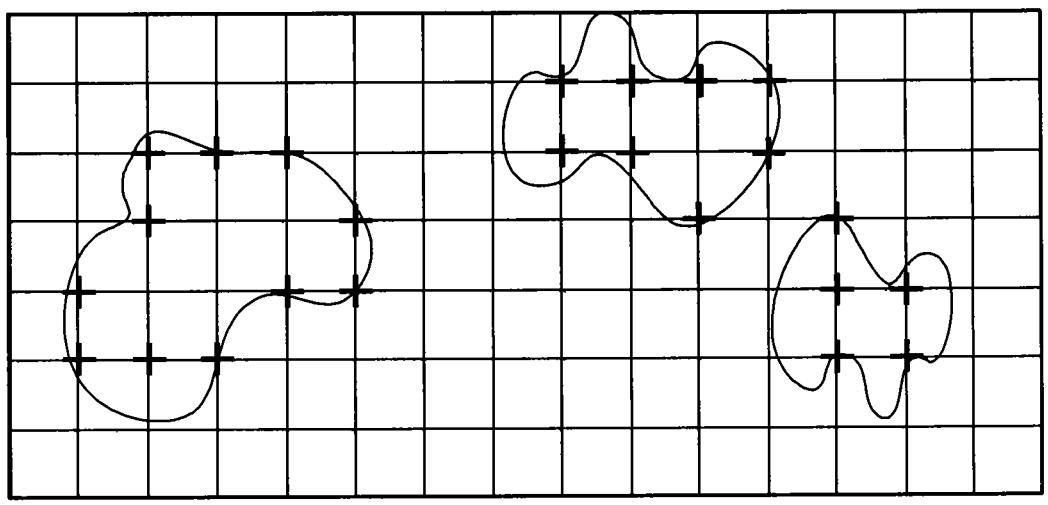
FIG. 9E is a diagram showing a grid point present on boundary areas between a base material and a pore.
Figure 9F:
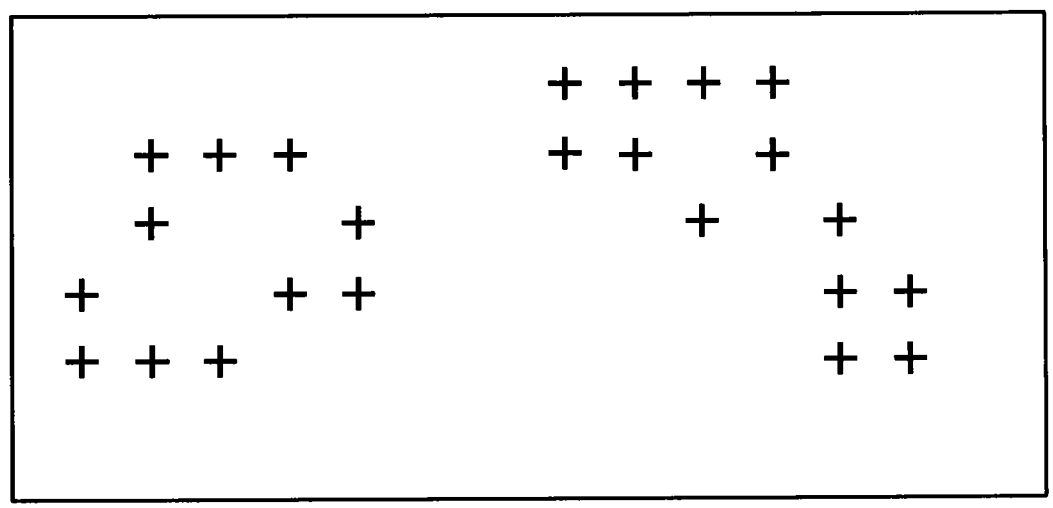
FIG. 9F is a diagram showing an example case in which grid points on the boundary areas are extracted.
Figure 9G:
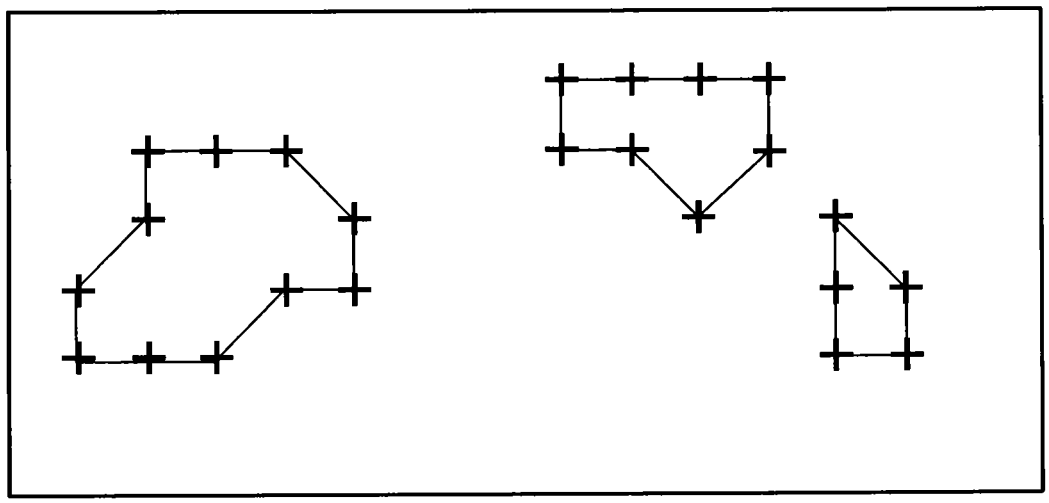
FIG. 9G is a diagram showing the grid points on boundary areas interconnected with each other.

Next, the processor 141 identifies successive grid points near an outer edge of the island of the base material (step S318). As shown in FIG. 9E, the processor 141 identifies, for example, grid points near an outer edge of each island. Thereafter, as shown in FIG. 9F, the processor 141 extracts the grid points near the outer edge. Moreover, as shown in FIG. 9G, a link of these grid points is obtained by the processor 141.

Next, the processor 141 determines whether or not the process for all tomographic images completes (step S319). When any unprocessed tomographic image remains, the processor 141 substitutes i+1 in i (step S320), and returns the process to the step S312. Thereafter, the processor 141 executes the same process on an i-th tomographic image.

Conversely, when determining as YES in the step S319, i.e., when determining that the modeling process of the base material has executed for all tomographic images, the processor 141 generates information that indicates a link of the grid points near an outer edge of each island between adjoining tomographic images (step S321). For example, the processor 141 associates grid points having relative positions adjoining to each other in the adjoining tomographic images.

Figure 10:
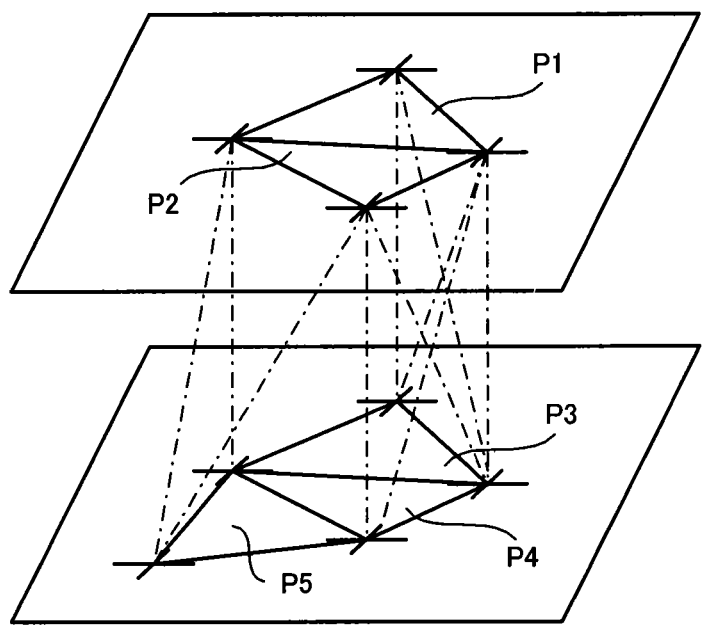
FIG. 10 is a diagram exemplifying a process of modeling a base material using triangular polygons.

Next, the processor 141 interconnects the grid points which are associated in the step S321 between the adjoining images. Accordingly, as is exemplified in FIG. 10, polygons, e.g., triangular polygons P1, . . . are defined (generated). That is, the processor 141 defines the triangular polygons P1, . . . which approximate an inner surface of the base material (step S322). The processor 141 executes this process for the grid points near the outer edges of all islands between the adjoining tomographic images.

The processor 141 completes the process of modeling the base material with the triangular polygons.

Next, the processor 141 draws the largest sphere in a pore around each grid point which is present within the pore of the three-dimensional model represented by the plurality of the tomographic images (step S323). Each sphere indicates a location where mercury would enter the pore.

A method of drawing the largest sphere is optional. For example, the processor 141 may set a sufficiently large radius R, and may execute a process of replacing R with r for all polygons when a minimum distance r between an arbitrary point over any polygon and a grid point is less than the radius R. As explained above, the processor 141 draws a sphere with a maximum size in the pore around each grid point which is present within the pore.

Figure 11:
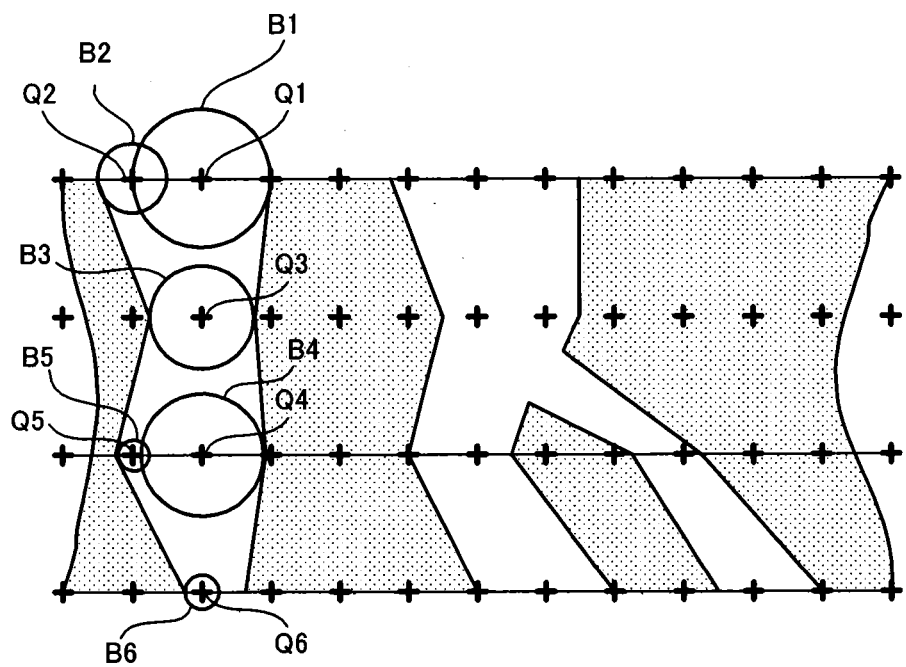
FIG. 11 is a diagram for explaining a process of generating grid points in a pore and of drawing the largest ball in the pore around each grid point.

More specifically, the processor 141 draws, for example, spheres B1 to B6 around respective grid points Q1 to Q6 shown in FIG. 11.

Subsequently, the processor 141 analyzes a network between the spheres drawn from one surface of the sample toward the interior thereof (step S324). That is, the processor 141 obtains information that indicates conditions of an overlap and a link of a sphere with another sphere from one surface side of the porous material.

Next, the processor 141 sorts the spheres obtained thus way in the order of a size (a radius), and associates the ID of the sphere and the size thereof with each other (step S325).

As explained above, the processor 141 models mercury being injected.

Next, the processor 141 obtains an amount of mercury entering from the one surface to the pore for each pressure P.

First, the processor 141 sets the pressure P to an initial value P0 to execute such a process (step S326).

Next, the processor 141 obtains a minimum diameter D0 of the pore that enables mercury to enter the pore at a pressure P (step S327).

In general, the minimum diameter of the pore that enables mercury to enter therein can be obtained as a formula (1) by a Washburn formula.

$$D0 = -4 \times \sigma \times \cos \theta / P \quad (1)$$

where:
D0: Minimum diameter of pore that enables mercury to enter;
σ: Surface tension of mercury (480 dyne cm$^{-1}$);
θ: Contact angle of mercury with wall surface of pore (in general, 140°); and
P: Pressure According to this embodiment, terms in consideration of a wettability value of the base material for mercury are added into the formula (1) to modify such a formula to a formula (2).

$$D0 = -4 \times \sigma \times \cos \theta / P - q(H0) \quad (2)$$

where:
H0: A surface energy measured by surface-energy measuring device 12 (mJ/m$^2$); and
q: A value corresponding to the surface energy H0 in FIG. 5.

According to such a modification of the formula, the surface energy of the base material is taken into consideration, and when the surface energy is low (wettability is good), a diameter D0 of the pore that enables mercury to enter becomes large.

In order to obtain the minimum diameter D0, first, the processor 141 refers to the database device 13, and reads a measured value H0 of a surface energy H corresponding to the sample subjected to an analysis.

Next, the processor 141 obtains a constant q (H0) depending on the wettability of mercury relative to the base material by substituting the measured surface energy H0 into a function q (see FIG. 5) obtained in advance.

Subsequently, the processor 141 obtains the minimum diameter D that enables mercury to enter from the formula (2) and given conditions.

Next, the processor 141 simulates, for example, an amount of entering mercury for each pore revealed on the one surface of the sample.

In order to do so, first of all, the processor 141 sets a pointer j that identifies the pore revealed on the one surface of the sample to be 1 based on the network of the spheres analyzed in the step S324 (step S328).

Next, the processor 141 specifies the sphere which enables mercury to enter for a j-th revealed pore. More specifically, the processor 141 traces spheres having a diameter of equal to or larger than D0 from the surface toward the deeper interior based on the network of the spheres analyzed in the step S324 (step S329). The processor 141 determines that a further entrance is disabled when a diameter of the linked sphere becomes smaller than the minimum entrance diameter D0. When there is a sphere having a diameter larger than the minimum entrance diameter D0 beyond a sphere having a diameter smaller than the minimum entrance diameter D0, the processor 141 determines that mercury would not enter such a larger sphere.

Accordingly, the processor 141 tracks spheres where mercury would enter at pressure of P0 for a pore revealed on the surface while identifying the spheres toward the deeper interior.

When the network of the spheres is branched within the interior, the processor 141 stores a location of a branched point in the memory 142, selects a route, and continues the process. When the processor 141 identifies a sphere having a diameter smaller than D0 in a route and reaches a dead end, the processor 141 selects a next route from the branched point stored in the memory 142, and continues the process.

Moreover, when the branched route is merged with an already processed network during the process, it is unnecessary for the processor 141 to further execute the process.

When completing the process for the revealed pore, the processor 141 determines whether or not there is any unprocessed revealed pore remaining (step S330). When any unprocessed revealed pore remains (step S330: No), the processor 141 updates j to j+1 (step S331), and processes a next revealed pore.

Figure 12:
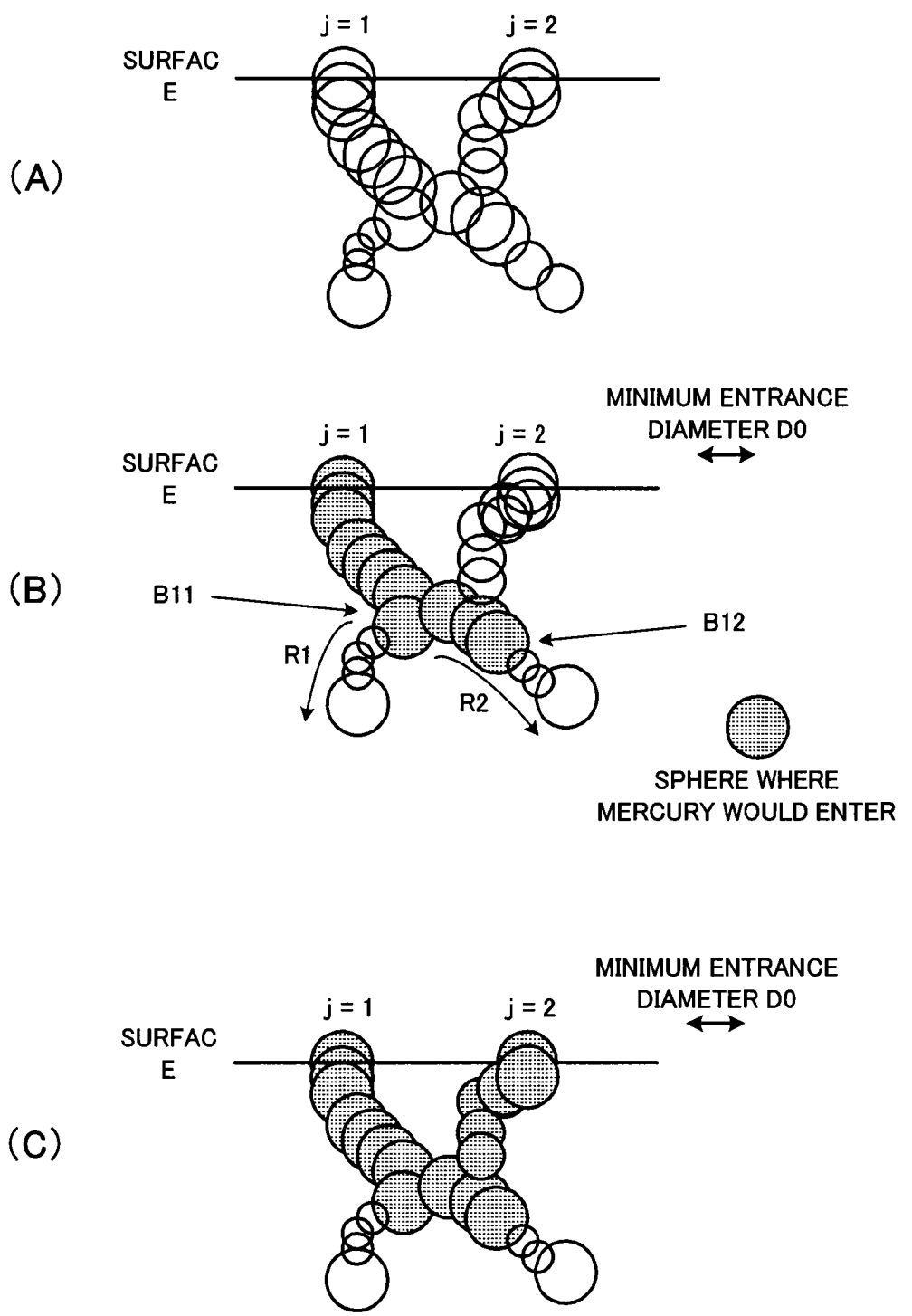
FIG. 12A is a diagram showing an example network of spheres drawn in pores.
FIGS. 12B and 12C are diagrams showing a simulation of a process of causing mercury to enter in a network of spheres.

For example, it is assumed that a network of spheres are generated as shown in FIG. 12A. The processor 141 tracks the spheres of a revealed pore that is j=1 successively from a surface side, and determines that mercury would successively enter as shown in FIG. 12B since the diameters of the tracked spheres are larger than D0. Branches are formed at a sphere B11, and the diameter of the sphere is smaller than the minimum entrance diameter D0, and thus the processor 141 determines, for a route R1, that mercury would not enter beyond such a sphere. Conversely, the processor 141 determines, for a route R2, that mercury would enter up to a sphere B12 but would not enter beyond such a sphere. Next, the processor 141 continues the process for the network of spheres connected to a revealed pore that is j=2 as shown in FIG. 12C while successively determining whether or not mercury would enter in respective spheres. The processor 141 terminates the process when a process-target sphere is merged with the processed network.

When determining that the process for all revealed pores completes with respect to a given pressure P (step S330: Yes), the processor 141 determines whether or not the process for all pressure P completes (step S332).

When any unprocessed pressure remains (step S332: No), the processor 141 updates the pressure P (step S333), and executes the same process.

When determining that the process for all pressure completes (step S332: Yes), the processor 141 obtains an amount of entering mercury (a volume thereof) for the spheres determined that mercury can enter therein at each pressure in consideration of the diameters and overlapping of the spheres. Moreover, the processor 141 obtains the number of spheres where mercury can enter for each size (step S334).

Figure 13:
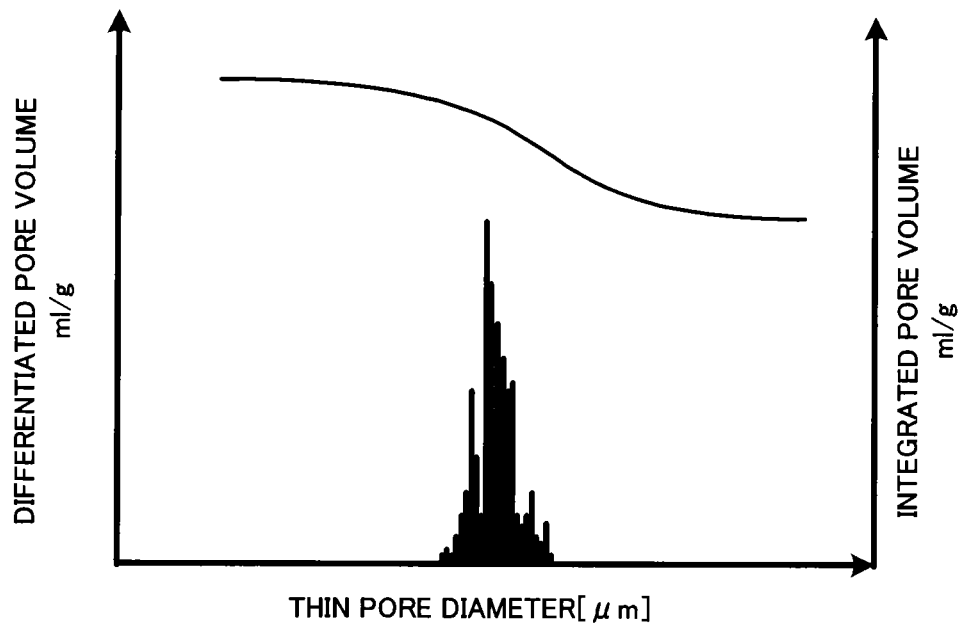
FIG. 13 is a diagram showing an example visualized simulation result.

Subsequently, the processor 141 stores, the database device 13, information, such as generated polygon models, the size distribution of the spheres (pores), information on a network of the spheres, an amount of entering mercury for each pressure, and the number of spheres where mercury can enter therein for each size (step S335). Furthermore, the processor 141 visualizes such pieces of information as is exemplified in FIG. 13, and outputs such pieces of information as needed in the manner of, for example, a display on the output device 143 (step S335).

According to this method, the simulation system 101 obtains, for the spheres where mercury enters, the minimum entrance diameter D of mercury for the spheres in consideration of not only the surface tension and the contact angle of mercury but also the surface energy (the wettability) of the base material. Hence, the simulation system 101 can obtain the minimum entrance diameter D more precisely in comparison with the method of obtaining the minimum entrance diameter D based on the formula (1) using only the surface tension σ and the contact angle θ of mercury and the pressure as subtractive terms. This enables the simulation system 101 to simulate a measurement of a pore diameter, etc., through the mercury intrusion method more precisely.

Modified Examples

The present invention is not limited to the above-explained embodiment, and various changes and modifications can be made.

For example, in the above-explained embodiment, the processor 141 expresses the base material using polygon models, generates the spheres in pores, and models mercury, but the modeling method is optional.

For example, in the above-explained embodiment, the processor 141 models the base material and the pores using triangular polygons, but such modeling can be made using other polygons, e.g., rectangular polygons. The processor can approximate an inner surface of the base material using pentagonal polygons. Moreover, the processor may put grid points in the interior of the base material, draw the largest circle in the interior of the base material around each grid point, and model the base material using these circles.

For example, the processor sets the grid points at the pore of a tomographic image formed by dividing the binarized tomographic image or the polygon model into n pieces in the thickness direction, and draws the largest circle in the interior of the pore around each grid point. The processor executes this process for n number of tomographic images.

Figure 14:
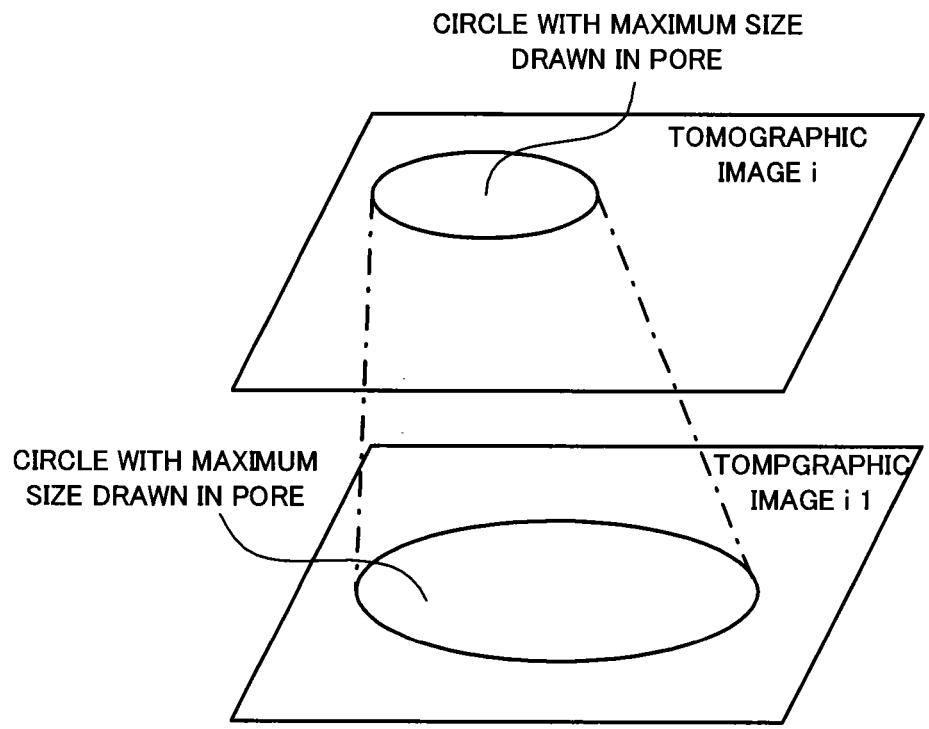
FIG. 14 is a diagram showing an example method of modeling a pore.

Subsequently, the processor may link the circles (the pores) of adjoining tomographic images as shown in FIG. 14, model the pore using a cylinder that interconnects the circle with another circle, and determine whether or not mercury can enter respective pores. Moreover, the processor may produce spheres in the cylinder, thereby modeling mercury.

As explained above, according to a simulation system of the above-explained embodiment, the surface energy (the wettability) of a sample is taken into consideration, and a simulation is enabled which reflects a physical property such that the greater the surface energy is (the lower the wettability is), the more mercury would easily enter in the pore.

A liquid subjected to a simulation according to the present invention is not limited to mercury. As long as a contact angle of a sample with the liquid and a surface tension of the liquid (the greater surface tension results in the better precision) are given, the present invention is applicable to any combination of the sample and the liquid.

The function of the simulation device 14 according to the above-explained embodiment can be implemented by an exclusive hardware or by a normal computer system.

For example, in the above-explained embodiment, a program which is stored in the memory 142 of the simulation device 14 may be stored in a computer-readable recording medium, such as a flexible disc, a CD-ROM (Compact Disk Read-Only Memory), a DVD (Digital Versatile Disk), or an MO (Magneto-Optical disk), and distributed, and installed in a computer to configure a device which executes the above-explained process.

Moreover, such a program may be stored in a disc device, etc., of a predetermined server device over a communication network like the Internet, and for example, superimposed on carrier waves and for example, downloaded to a computer.

Moreover, the above-explained process can be accomplished by activating and running the program while transferring the program via the communication network.

Furthermore, the above-explained process can be accomplished by causing a server device to execute all of or a part of the program, and by causing a computer to execute the program while exchanging information obtained from the process executed by the server device over a communication network.

When, for example, an OS (Operating System) bears and realizes the above-explained function, or when the OS and an application cooperatively realize the above-explained function, only portions other than the OS may be stored in a medium for distribution, and, for example, may be downloaded to a computer.

INDUSTRIAL APPLICABILITY

The simulation device, the simulation system, the simulation method, and the program according to the present invention are suitable for simulating a liquid entering a porous material.

DESCRIPTION OF REFERENCE NUMERALS

101: Simulation system
11: X-ray CT device
12: Surface-energy measuring device
13: Database device
14: Simulation device
141: Processor
142: Memory
143: Output device
144: Input device
145: Communication device
NW: Communication network
P1, P2, P3, P4, P5: Polygon
Q1, Q2, Q3, Q4, Q5, Q6: Grid point
B1, B2, B3, B4, B5, B6, B11, B12: Sphere
R1, R2: Route

The invention claimed is:

1. A simulation method, comprising:
   processing a tomographic image of a sample such that an internal structure of the sample is modeled;
   obtaining a minimum diameter of a pore of the sample which allows a predetermined liquid to enter at a predetermined pressure; and
   simulating a condition in which the liquid enters in the pore from a surface of the sample based on a diameter of the pore of the modeled sample and the minimum diameter,
   wherein the obtaining of the minimum diameter comprises obtaining a minimum diameter D0 of the pore which allows the liquid to enter, based on a formula:

$$D0 = -4 \times \sigma \times \cos\theta / P - q(H0)$$

where $\sigma$ is a surface tension of the liquid, $\theta$ is a contact angle of the liquid with a wall surface of the pore, P is a pressure of the liquid, H0 is a surface energy of the sample, and q is a function based on the surface energy of the sample.

2. The simulation method according to claim 1, wherein the simulating comprises:
   specifying a plurality of spheres in a pore of the modeled sample;
   selecting spheres successive from a surface of the sample and having a diameter equal to or larger than the minimum diameter; and
   calculating an average diameter of the pore of the sample and an amount of the liquid flown into the pore of the sample based on a volume of the selected successive spheres in the pore and a number of the successive spheres for each size.

3. The simulation method according to claim 2, wherein the liquid is mercury.

4. The simulation method according to claim 1, wherein the liquid is mercury.

* * * * *